(12) United States Patent
Kothandaraman et al.

(10) Patent No.: US 9,095,724 B2
(45) Date of Patent: Aug. 4, 2015

(54) NEUROMODULATION SYSTEM WITH DUAL TELEMETRY SYSTEM

(71) Applicant: BOSTON SCIENTIFIC NEUROMODULATION CORPORATION, Valencia, CA (US)

(72) Inventors: Sridhar Kothandaraman, Valencia, CA (US); Que T. Doan, West Hills, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/188,535

(22) Filed: Feb. 24, 2014

(65) Prior Publication Data
US 2014/0243927 A1     Aug. 28, 2014

Related U.S. Application Data

(60) Provisional application No. 61/768,831, filed on Feb. 25, 2013.

(51) Int. Cl.
*A61N 1/372* (2006.01)
*A61N 1/08* (2006.01)
*A61N 1/36* (2006.01)

(52) U.S. Cl.
CPC .......... *A61N 1/37217* (2013.01); *A61N 1/3605* (2013.01); *A61N 1/37252* (2013.01); *A61N 1/3727* (2013.01)

(58) Field of Classification Search
None
See application file for complete search history.

(56) References Cited

U.S. PATENT DOCUMENTS

| | | | |
|---|---|---|---|
| 5,342,408 A * | 8/1994 | deCoriolis et al. | 607/32 |
| 6,443,891 B1 * | 9/2002 | Grevious | 600/302 |
| 6,516,227 B1 | 2/2003 | Meadows et al. | |
| 6,895,280 B2 | 5/2005 | Meadows et al. | |
| 6,993,384 B2 | 1/2006 | Bradley et al. | |
| 7,539,538 B2 | 5/2009 | Parramon et al. | |
| 2010/0010566 A1 | 1/2010 | Thacker et al. | |
| 2010/0121409 A1 | 5/2010 | Kothandaraman et al. | |

* cited by examiner

*Primary Examiner* — Brian T Gedeon
(74) *Attorney, Agent, or Firm* — Schwegman Lundberg & Woessner, P.A.

(57) ABSTRACT

An implantable neuromodulation device includes a plurality of electrical terminals configured for being respectively coupled to a plurality of electrodes; analog output circuitry configured for delivering electrical modulation energy to the electrical terminals in accordance with programming data from a first external control device; a low-speed telemetry system configured for receiving the programming data; a high-speed telemetry system configured for receiving non-programming data from a second external control device; and memory configured for storing the programming data and the non-programming data. The low-speed telemetry system has a data transfer rate in the range of 2-800 kbits/sec, and the high-speed telemetry system has a data transfer rate in the range of 1-50 Mbits/sec. The high-speed telemetry system may have a greater telemetry range than the low-speed telemetry system.

16 Claims, 7 Drawing Sheets

NEUROMODULATION SYSTEM WITH DUAL TELEMETRY SYSTEM

RELATED APPLICATION DATA

The present application claims the benefit under 35 U.S.C. §119 to U.S. provisional patent application Ser. No. 61/768,831, filed Feb. 25, 2013. The foregoing application is hereby incorporated by reference into the present application in its entirety.

FIELD OF THE INVENTION

The present inventions relate to tissue modulation systems, and more particularly, to systems and methods for transmitting data to, and receiving data from, an implantable neuromodulation device.

BACKGROUND OF THE INVENTION

Implantable neuromodulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of spinal modulation has begun to expand to additional applications, such as angina pectoris and incontinence. Deep Brain Stimulation (DBS) has also been applied therapeutically for well over a decade for the treatment of refractory Parkinson's Disease, and DBS has also recently been applied in additional areas, such as essential tremor and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems such as the Freehand system by NeuroControl (Cleveland, Ohio) have been applied to restore some functionality to paralyzed extremities in spinal cord injury patients.

Each of these implantable neuromodulation systems typically includes one or more electrode carrying modulation leads, which are implanted at the desired stimulation site, and a neuromodulation device implanted remotely from the stimulation site, but coupled either directly to the modulation lead(s) or indirectly to the modulation lead(s) via a lead extension. Thus, electrical pulses can be delivered from the neuromodulation device to the electrode(s) to modulate a volume of tissue in accordance with a set of modulation parameters and provide the desired efficacious therapy to the patient. For example, electrical energy conveyed between at least one cathodic electrode and at least one anodic electrode creates an electrical field, which when strong enough, depolarizes (or "stimulates") the neurons beyond a threshold level, thereby inducing the firing of action potentials (APs) that propagate along the neural fibers. A typical modulation parameter set may include the electrodes that are sourcing (anodes) or returning (cathodes) the modulating current at any given time, as well as the amplitude, duration, and rate of the electrical modulation pulses.

The neuromodulation system may further comprise a handheld patient programmer to remotely instruct the neuromodulation device to generate electrical modulation pulses in accordance with selected modulation parameters. The handheld programmer in the form of a remote control (RC) may, itself, be programmed by a clinician, for example, by using a clinician's programmer (CP), which typically includes a general purpose computer, such as a laptop, with a programming software package installed thereon.

The RC and/or the CP communicate telemetrically with the neuromodulation device. Current neuromodulation systems use a single telemetry system where the range is typically limited to a few feet and the data transfer rate is relatively low. The limited range of the telemetry system allows the neuromodulation device to be programmed, while avoiding interference from spurious/malicious communications with the implanted device. The relatively low data transfer rate is sufficient for transmitting a small amount of programming data to and from the implanted neuromodulation device.

However, there is a need to store large amounts of data in the implanted device to enable seamless programming of the device when programmed using different external systems. In one example, for DBS, the pre-op MRI and the post-op CT are used to identify brain structures and the lead position inside the brain. These images are then manipulated in a process called registration to identify patient-specific brain structures and to transform a generic brain atlas into a patient-specific brain atlas. The MRI and CT data are typically large datasets that are retrieved and stored from radiography CDs onto external programming systems. If the patient is seen by a different system/clinic, this information is not readily available. It is practically impossible to transfer this large amount of data to the implanted neuromodulation device with the current low speed, short range telemetry systems.

There, thus, remains a need for a high speed telemetry system that will enable the quick transfer of large amounts of data to and from the neuromodulation device for use by any external device.

SUMMARY OF THE INVENTION

In accordance with a first aspect of the present inventions, an implantable neuromodulation device is provided. The device includes a plurality of electrical terminals configured for being respectively coupled to a plurality of electrodes; analog output circuitry configured for delivering electrical modulation energy to the electrical terminals in accordance with programming data from a first external control device; a low-speed telemetry system configured for receiving the programming data; a high-speed telemetry system configured for receiving non-programming data (e.g., Magnetic Resonance Image (MRI) data, Computed Tomography (CT) data, clinical effects data, brain atlas transformation data, program usage data, battery history data, electrical parameter measurement data, lead configuration data, electrode configuration data, and/or safety limit data) from a second external control device; and memory configured for storing the programming data and the non-programming data. The first external control device and the second external control device may be the same external control device. The low-speed telemetry system may be configured for transmitting the stored programming data to the first external control device, and the high-speed telemetry system may be configured for transmitting the stored non-programming data to the second external control device.

In accordance with a second aspect of the present inventions, a neuromodulation system is provided. The system includes a first external control device configured for transmitting programming data and a second external control device configured for transmitting non-programming data (e.g., Magnetic Resonance Image (MRI) data, Computed Tomography (CT) data, clinical effects data, brain atlas transformation data, program usage data, battery history data, electrical parameter measurement data, lead configuration data, electrode configuration data, and/or safety limit data). The first external control device and the second external control device may be the same external control device. The system further includes a plurality of electrodes, and an implantable neuromodulation device comprising a plurality of electrical terminals coupled to the plurality of electrodes, analog output circuitry configured for delivering electrical modulation energy to the electrical terminals in accordance with the programming data from the first external control device, a low-speed telemetry system configured for receiving the programming data, a high-speed telemetry system configured for receiving the non-programming data from the second external control device, and memory configured for storing the programming data and the non-programming data. The low-speed telemetry system may be configured for transmitting the stored programming data to the first external control device, and the high-speed telemetry system may be configured for transmitting the stored non-programming data to the second external control device.

In accordance with a third aspect of the present inventions, a method of operating an implantable neuromodulation device in communication with a first external control device and a second external control device is provided. The first external control device and the second external control device may be the same external control device. The method includes transmitting programming data to, or receiving programming data from, the first external control device using a low-speed telemetry system. The programming data may be transmitted or received at a data transfer rate typically in the range of 2-800 kbits/sec. The method further includes transmitting non-programming data (e.g., Magnetic Resonance Image (MRI) data, Computed Tomography (CT) data, clinical effects data, brain atlas transformation data, program usage data, battery history data, electrical parameter measurement data, lead configuration data, electrode configuration data, and/or safety limit data) to, or receiving non-programming data from, the second external control device using a high-speed telemetry system. The non-programming data may be transmitted or received at a data transfer rate typically in the range of 1-50 Mbits/sec. The method further includes delivering electrical modulation energy to a plurality of electrical terminals in accordance with the programming data.

The low-speed telemetry system may have a data transfer rate in the range of 2-800 kbits/sec, and the high-speed telemetry system may have a data transfer rate in the range of 1-50 Mbits/sec. The low-speed telemetry system may have a first telemetry range, and the high-speed telemetry system may have a second telemetry range greater than the first telemetry range. The first telemetry range may be 0.1-6 feet, and the second telemetry range may be greater than 6 feet. The second telemetry range may be further extended with the use of cellular networks.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings.

Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal column modulation (SCM) system. However, it is to be understood that the while the invention lends itself well to applications in SCM, the invention, in its broadest aspects, may not be so limited. Rather, the invention may be used with any type of implantable electrical circuitry used to modulate tissue. For example, the present invention may be used as part of a pacemaker, a defibrillator, a cochlear modulator device, a retinal modulator device, a modulator device configured to produce coordinated limb movement, a cortical modulator device, a deep brain modulator device, peripheral nerve modulator device, micromodulator device, or in any other tissue modulator device configured to treat urinary incontinence, sleep apnea, shoulder sublaxation, headache, etc.

Figure 1:
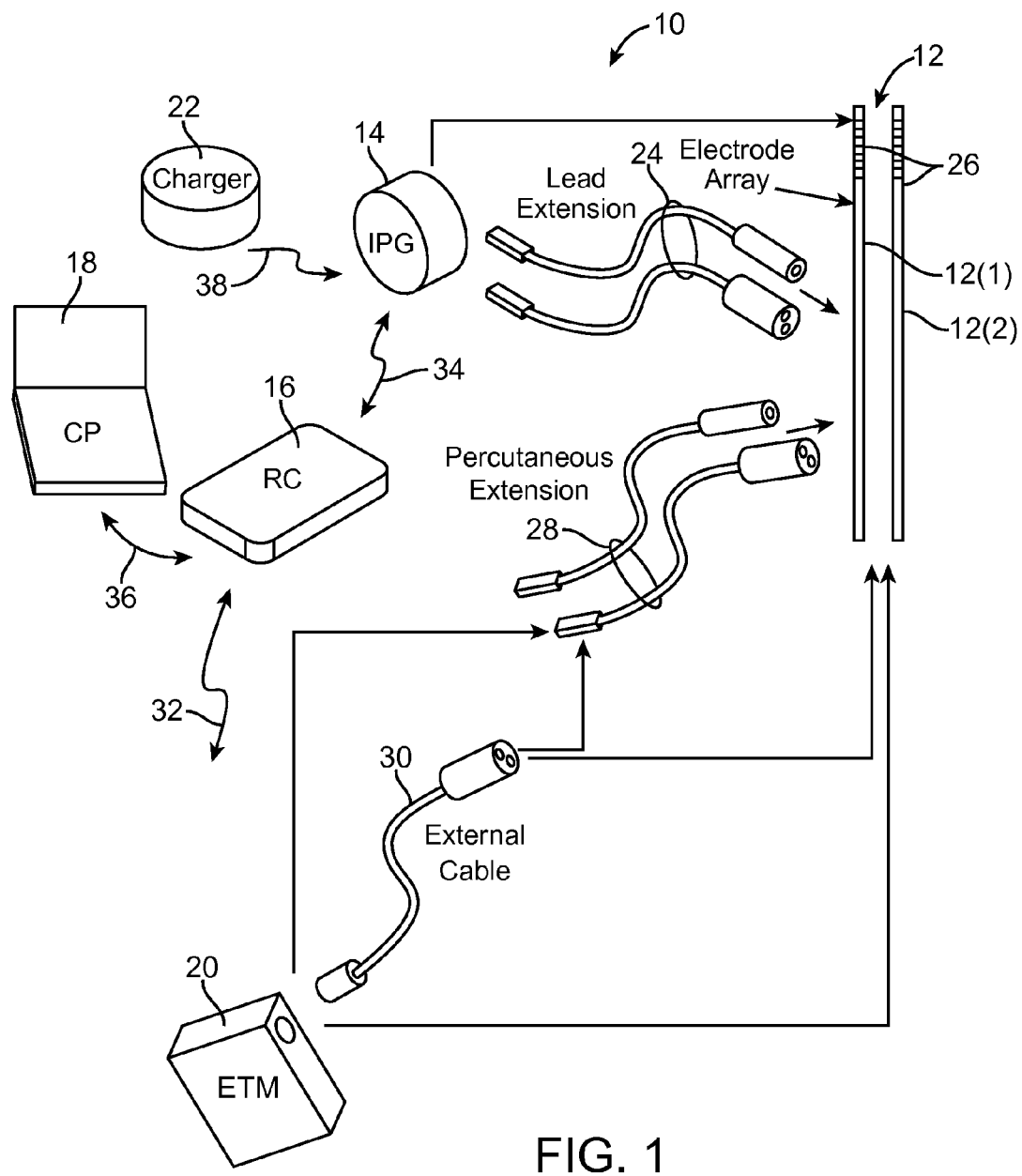
FIG. 1 is plan view of one embodiment of a spinal column modulation (SCM) system arranged in accordance with the present inventions.

Turning first to FIG. 1, an exemplary SCM system 10 generally includes one or more (in this case, two) implantable modulation leads 12(1) and 12(2), a fully implantable modulator (IPG) 14, an External Trial Modulator (ETM) 20, and an external charger 22. The system 10 also includes external control devices, such as an external remote controller RC 16 and a clinician's programmer (CP) 18.

The IPG 14 is physically connected via one or more percutaneous lead extensions 24 to the modulation leads 12, which carry a plurality of electrodes 26 arranged in an array. In the illustrated embodiment, the modulation leads 12 are percutaneous leads, and to this end, the electrodes 26 are arranged in-line along the modulation leads 12. In alternative embodiments, the electrodes 26 may be arranged in a two-dimensional pattern on a single paddle lead. As will be described in further detail below, the IPG 14 includes pulse generation circuitry that delivers the electrical modulation energy in the form of an electrical pulse train to the electrode array 26 in accordance with a set of modulation parameters.

The ETM 20 may also be physically connected via percutaneous lead extensions 28 and an external cable 30 to the modulation leads 12. The ETM 20, which has similar pulse generation circuitry to that of the IPG 14, also delivers electrical modulation energy in the form of an electrical pulse train to the electrode array 26. The major difference between the ETM 20 and the IPG 14 is that the ETM 20 is a non-implantable device that is used on a trial basis after the modulation leads 12 have been implanted and prior to implantation of the IPG 14, to test the responsiveness of the modulation that is to be provided. Thus, any functions described herein with respect to the IPG 14 can likewise be performed with respect to the ETM 20.

The RC 16 may be used to telemetrically control the ETM 20 via a bi-directional RF communications link 32. Once the IPG 14 and modulation leads 12 are implanted, the RC 16 may be used to telemetrically control the IPG 14 via a bi-directional RF communications link 34. Such control allows the IPG 14 to be turned on or off and to be programmed with different modulation parameter sets. The IPG 14 may also be operated to modify the programmed modulation parameters to actively control the characteristics of the electrical modulation energy output by the IPG 14.

The CP 18 provides clinician detailed modulation parameters for programming the IPG 14 and ETM 20 in the operating room and in follow-up sessions. The CP 18 may perform this function by indirectly communicating with the IPG 14 or ETM 20, through the RC 16, via an IR communications link 36. Alternatively, the CP 18 may directly communicate with the IPG 14 or ETM 20 via an RF communications link (not shown).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

For purposes of brevity, the details of the RC 16, CP 18, ETM 20, and external charger 22 will not be described herein. Details of exemplary embodiments of these devices are disclosed in U.S. Pat. No. 6,895,280, which is expressly incorporated herein by reference.

Figure 2:
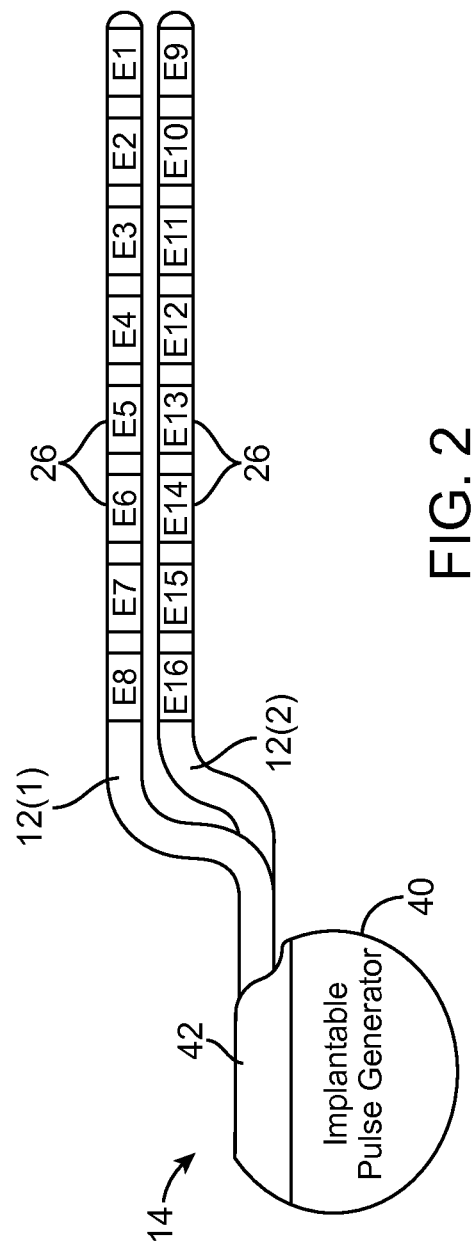
FIG. 2 is a profile view of an implantable pulse generator (IPG) used in the SCM system of FIG. 1.

Referring now to FIG. 2, the external features of the modulation leads 12 and the IPG 14 will be briefly described. One of the modulation leads 12(1) has eight electrodes 26 (labeled E1-E8), and the other modulation lead 12(2) has eight electrodes 26 (labeled E9-E16). The actual number and shape of leads and electrodes will, of course, vary according to the intended application. The IPG 14 comprises an outer case 40 for housing the electronic and other components (described in further detail below), and a connector 42 to which the proximal ends of the modulation leads 12 mate in a manner that electrically couples the electrodes 26 to the electronics within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

As will be described in further detail below, the IPG 14 includes pulse generation circuitry that provides electrical modulation energy to the electrodes 26 in accordance with a set of modulation parameters. Such parameters may comprise electrode combinations, which define the electrodes that are activated as anodes (positive), cathodes (negative), and turned off (zero), and electrical pulse parameters, which define the pulse amplitude (measured in milliamps or volts depending on whether the IPG 14 supplies constant current or constant voltage to the electrodes), pulse width (measured in microseconds), pulse rate (measured in pulses per second), duty cycle (pulse width divided by cycle duration), burst rate (measured as the modulation energy on duration X and modulation energy off duration Y), and pulse shape.

With respect to the pulse patterns provided during operation of the SCM system 10, electrodes that are selected to transmit or receive electrical energy are referred to herein as "activated," while electrodes that are not selected to transmit or receive electrical energy are referred to herein as "non-activated." Electrical energy delivery will occur between two (or more) electrodes, one of which may be the IPG case 40, so that the electrical current has a path from the energy source contained within the IPG case 40 to the tissue and a sink path from the tissue to the energy source contained within the case 40. Electrical energy may be transmitted to the tissue in a monopolar or multipolar (e.g., bipolar, tripolar, etc.) fashion.

Monopolar delivery occurs when a selected one or more of the lead electrodes 26 is activated along with the case 40 of the IPG 14, so that electrical energy is transmitted between the selected electrode 26 and case 40. Monopolar delivery may also occur when one or more of the lead electrodes 26 are activated along with a large group of lead electrodes located remotely from the one or more lead electrodes 26 so as to create a monopolar effect; that is, electrical energy is conveyed from the one or more lead electrodes 26 in a relatively isotropic manner. Bipolar delivery occurs when two of the lead electrodes 26 are activated as anode and cathode, so that electrical energy is transmitted between the selected electrodes 26. Tripolar delivery occurs when three of the lead electrodes 26 are activated, two as anodes and the remaining one as a cathode, or two as cathodes and the remaining one as an anode.

The electrical energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) modulation pulse and an anodic (positive) recharge pulse that is generated after the modulation pulse to prevent direct current charge transfer through the tissue, thereby avoiding electrode degradation and cell trauma.

That is, charge is conveyed through the electrode-tissue interface via current at an electrode during a modulation period (the length of the modulation pulse), and then pulled back off the electrode-tissue interface via an oppositely polarized current at the same electrode during a recharge period (the length of the recharge pulse). The recharge pulse may be active, in which case, the electrical current is actively conveyed through the electrode via current or voltage sources, or the recharge pulse may be passive, in which case, the electrical current may be passively conveyed through the electrode via redistribution of the charge flowing from coupling capacitances present in the circuit.

Figure 3:
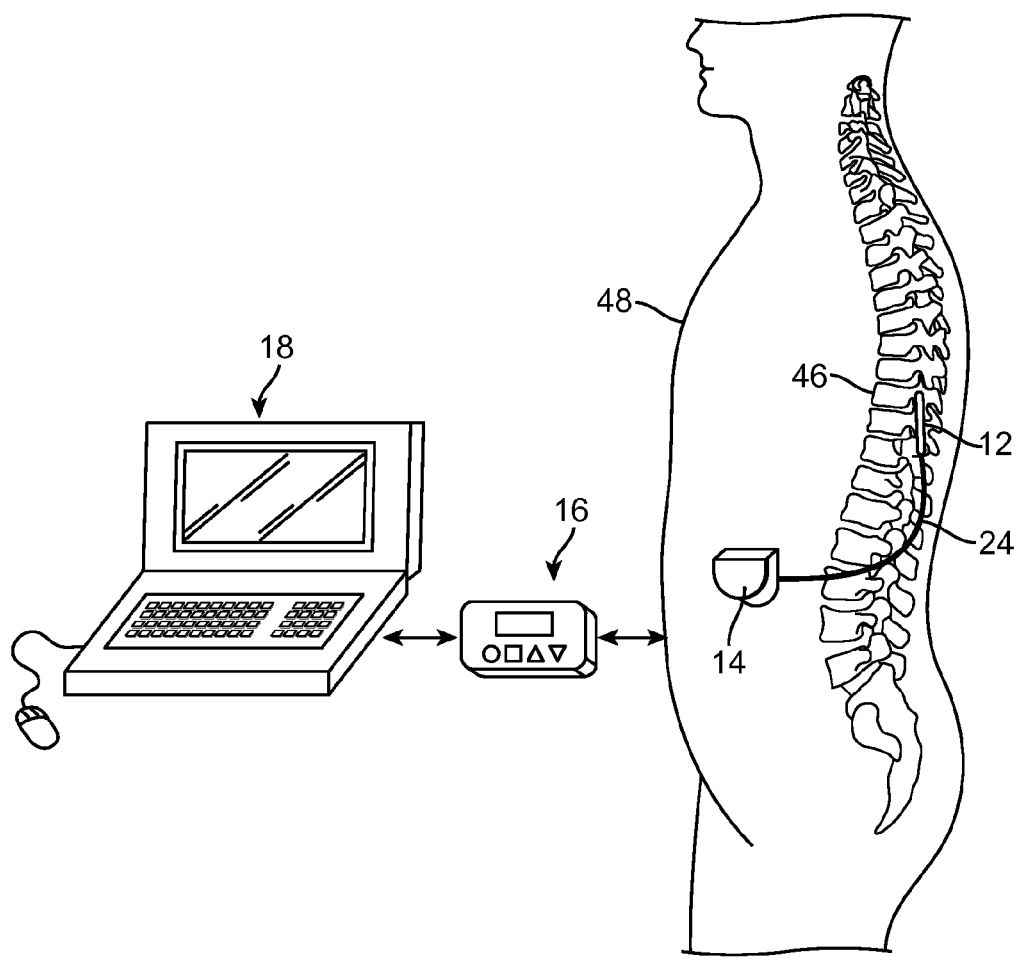
FIG. 3 is a plan view of the SCM system of FIG. 1 in use with a patient.

As shown in FIG. 3, the modulation leads 12 are implanted within the spinal column 46 of a patient 48. The preferred placement of the stimulation leads 12 is adjacent, i.e., resting near, or upon the dura, adjacent to the spinal cord area to be stimulated. Due to the lack of space near the location where the electrode leads 12 exit the spinal column 46, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the electrode leads 12. As there shown, the CP 18 communicates with the IPG 14 via the RC 16.

Figure 4:
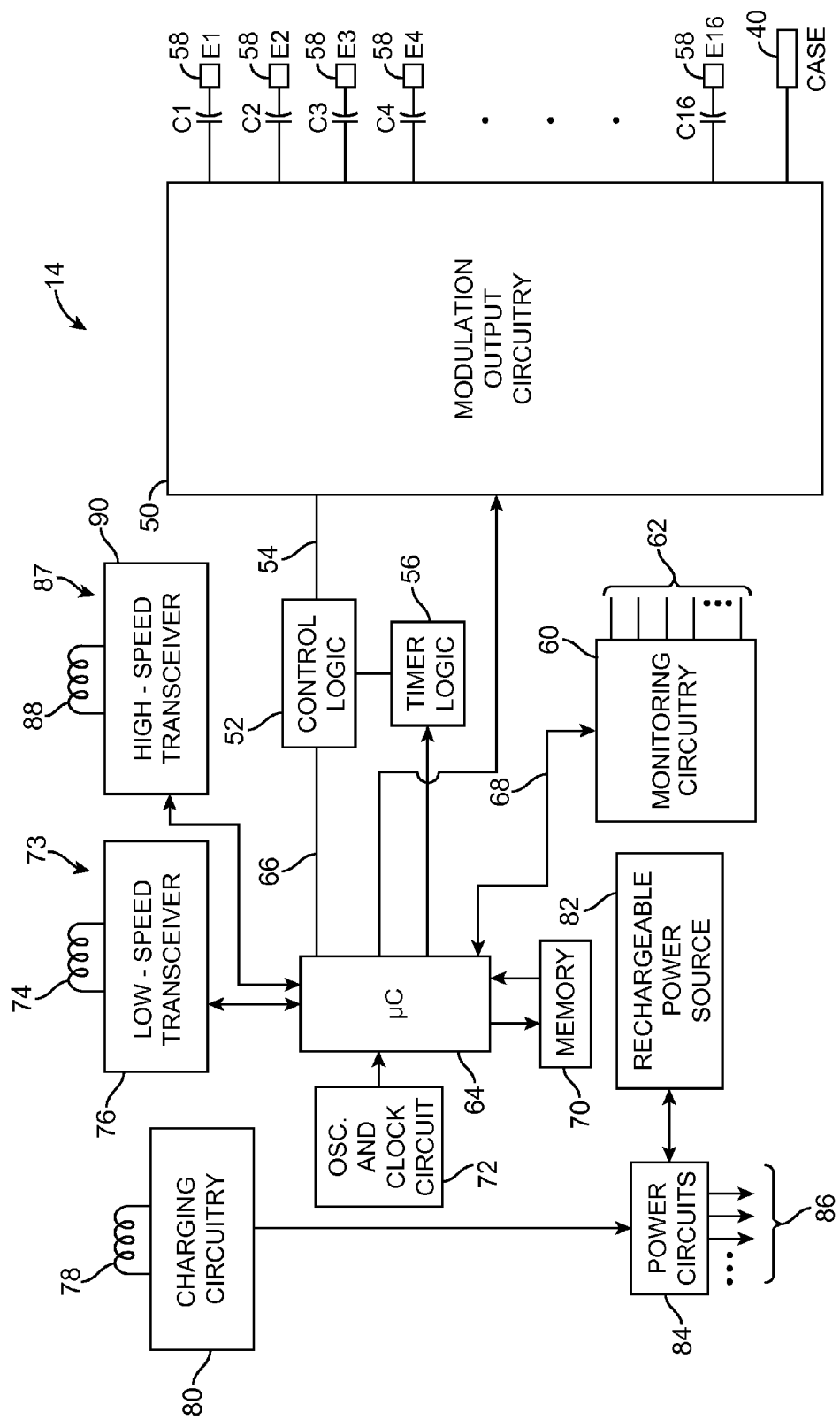
FIG. 4 is a block diagram of the internal components of the IPG of FIG. 2.

Turning next to FIG. 4, one exemplary embodiment of the IPG 14 will now be described. The IPG 14 includes analog modulation output circuitry 50 configured for generating electrical modulation energy in accordance with an electrical pulse train having a specified pulse amplitude, pulse rate, pulse width, duty cycle, burst rate, and shape under control of control logic 52 over data bus 54. Control of the pulse rate and duration is facilitated by analog circuitry, or digital timer logic circuitry 56 controlling the analog circuitry, and which may have a suitable resolution, e.g., 10 µs. In alternative embodiments, a continuous modulating waveform may be generated by the modulation output circuitry 50 in a manner described in U.S. Provisional Patent Application Ser. No. 61/646,773, entitled "System and Method for Shaped Phased Current Delivery," which is expressly incorporated herein by reference. The modulation energy generated by the modulation output circuitry 50 is output via capacitors C1-C16 to electrical terminals 58 configured for being coupled to electrodes E1-E16.

The modulation output circuitry 50 may either comprise independently controlled current sources for providing stimulation pulses of a specified and known amperage to or from the electrical terminals 58, or independently controlled voltage sources for providing stimulation pulses of a specified and known voltage at the electrical terminals 58 or to multiplexed current or voltage sources that are then connected to the electrical terminals 58. The operation of this modulation output circuitry 50, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference.

The IPG 14 also comprises monitoring circuitry 60 for monitoring the status of various nodes or other points 62 throughout the IPG 14, e.g., power supply voltages, temperature, battery voltage, and the like. The monitoring circuitry 60 is also configured for measuring electrical parameter data (e.g., electrode impedance and/or electrode field potential). The IPG 14 further comprises processing circuitry in the form of a microcontroller (µC) 64 that controls the control logic 52 over data bus 66, and obtains status data from the monitoring circuitry 60 via data bus 68. The microcontroller 64 additionally controls the timer logic 56. The IPG 14 further comprises memory 70 and oscillator and clock circuit 72 coupled to the microcontroller 64. The microcontroller 64, in combination with the memory 70 and oscillator and clock circuit 72, thus comprise a microprocessor system that carries out a program function in accordance with a suitable program stored in the memory 70. Alternatively, for some applications, the function provided by the microprocessor system may be carried out by a suitable state machine.

Thus, the microcontroller 64 generates the necessary control and status signals, which allow the microcontroller 64 to control the operation of the IPG 14 in accordance with a selected operating program and modulation parameters. In controlling the operation of the IPG 14, the microcontroller 64 is able to individually generate electrical energy at the electrodes 26 using the modulation output circuitry 50, in combination with the control logic 52 and timer logic 56, thereby allowing each electrode 26 to be paired or grouped with other electrodes 26, including the monopolar case electrode, to control the polarity, pulse amplitude, pulse rate, pulse width, and pulse duty cycle through which the electrical energy is provided.

The IPG 14 further comprises a bi-directional, low-speed telemetry system 73 for transmitting and receiving programming data (e.g., the operating program and/or modulation parameters) to and from the RC 16 and/or CP 18. Because the programming data is a relatively small data set, the data transfer rate of the low-speed telemetry system 73 may be relatively low. The low-speed telemetry system 73 comprises an alternating current (AC) coil 74 and a low speed transceiver 76. The AC coil 74 is configured for receiving the programming data in an appropriate modulated carrier signal, and the low speed transceiver 76 is configured for demodulating the carrier signal it receives through the AC coil 74 to recover the programming data. The programming data is then stored within the memory 70, or within other memory elements (not shown) distributed throughout the IPG 14. The AC coil 74 is also configured for sending informational data sensed through the monitoring circuitry 60 to the RC 16 and/or CP 18.

The back telemetry features of the IPG 14 also allow its status to be checked. For example, when the RC 16 and/or CP 18 initiates a programming session with the IPG 14, the capacity of the battery is telemetered, so that the RC 16 and/or CP 18 can calculate the estimated time to recharge. Any changes made to the current stimulus parameters are confirmed through back telemetry, thereby assuring that such changes have been correctly received and implemented within the implant system. Moreover, upon interrogation by the RC 16 and/or CP 18, all programmable settings stored within the IPG 14 may be uploaded to the RC 16 and/or CP 18. To this end, the low speed transceiver 76 is configured for modulating the status data in an appropriate modulated carrier signal, and the AC coil 74 is configured for transmitting the modulated carrier signal.

The IPG 14 further comprises a bi-directional, high-speed telemetry system 87 for transmitting and receiving non-programming data to and from the RC 16 and/or CP 18. Non-programming data may include Magnetic Resonance Image (MRI) data, Computed Tomography (CT) data, clinical effects data, brain atlas transformation data, program usage data, battery history data, electrical parameter measurement data, lead configuration data, electrode configuration data, safety limit data, or the like. Because the non-programming data may be a relatively large data set, the high speed telemetry system 87 may have a relatively high data transfer rate. Due to the higher data transfer rate, the high-speed telemetry system 87 consumes power at a higher rate than the low-speed telemetry system. As such, the high-speed telemetry system 87 may be used for only short durations of time.

The high speed telemetry system includes an AC coil 88 and a high speed transceiver 90. The AC coil 88 is configured for receiving the non-programming data in an appropriate modulated carrier signal, and the high speed transceiver 90 is configured for demodulating the carrier signal it receives through the AC coil 88 to recover the non-programming data. The non-programming data is then stored within the memory 70, or within other memory elements (not shown) distributed throughout the IPG 14. The AC coil 88 is also configured for sending non-programming data to the RC 16 and/or the CP 18. Upon interrogation by the RC 16 and/or the CP 18, non-programming data stored within the IPG 14 may be uploaded to the RC 16 and/or CP 18. To this end, the high speed transceiver 90 is configured for modulating the non-programming data in an appropriate modulated carrier signal, and the AC coil 88 is configured for transmitting the modulated carrier signal. Storing such non-programming data in the IPG 14 facilitates retrieval of such data when the patient goes to a new clinic/facility for a programming procedure.

The data transfer rate of the high-speed telemetry system 87 is higher than that of the low-speed telemetry system 73. For example, the data transfer rate of the high-speed telemetry system 87 may be in the range of 1-50 Mbits/sec, while the data transfer rate of the low-speed telemetry system 73 may be in the range of 2-800 kbits/sec. The high-speed telemetry system 87 may have a greater range than the low-speed telemetry system 73. For example, the range of the high-speed telemetry system 87 may be greater than 6 feet, while the range of the low-speed telemetry system 73 may be 0.1-6 feet. Alternatively, the low-speed telemetry system 73 may have a greater range than the high-speed telemetry system 87, or both telemetry systems may have a shorter range, or both telemetry systems may have a higher range. While a greater range may provide more convenience, one disadvantage of a higher range telemetry system is that more noise may be introduced. Further, a higher range telemetry system may be less secure. Due to security considerations, programming data is typically transmitted over a short range telemetry system.

Either one or both of the CP 18 and the RC 16 may be configured for transmitting the programming data to the IPG 14. Similarly, either one or both of the CP 18 and the RC 16 may be configured for transmitting the non-programming data to the IPG 14. Both the programming and non-programming data may be received from the CP 18. Alternatively, both the programming and non-programming data may be received from the RC 16. As such, the CP 18 and/or the RC 16 may include both a low-speed telemetry system and a high-speed telemetry system, as discussed in greater detail below. Alternatively, the CP 18 and the RC 16 may include only a single telemetry system, and the SCM system 10 may include a dual telemetry external bridge device (not shown) for facilitating communication between the CP 18, the RC 16, and the IPG 14.

The IPG 14 further comprises a rechargeable power source 82 and power circuits 84 for providing the operating power to the IPG 14. The rechargeable power source 82 may, e.g., comprise a lithium-ion or lithium-ion polymer battery. The rechargeable battery 82 provides an unregulated voltage to the power circuits 84. The power circuits 84, in turn, generate the various voltages 86, some of which are regulated and some of which are not, as needed by the various circuits located within the IPG 14. The rechargeable power source 82 is recharged using rectified AC power (or DC power converted from AC power through other means, e.g., efficient AC-to-DC converter circuits, also known as "inverter circuits") received by an AC receiving coil 78 and charging circuitry 80. To recharge the power source 82, the external charger 22 (shown in FIG. 1), which generates the AC magnetic field, is placed against, or otherwise adjacent, to the patient's skin over the implanted IPG 14. The AC magnetic field emitted by the external charger 22 induces AC currents in the AC receiving coil 78. The charging circuitry 80 rectifies the AC current to produce DC current, which is used to charge the power source 82. While the AC receiving coil 78 is described as a dedicated charging coil for wirelessly receiving charging energy from the external device, it should be appreciated that the AC receiving coil 78 and the charging circuitry 80 may be incorporated into the high-speed telemetry system 87 or the low-speed telemetry system 73. For example, the low-speed transceiver 76 may additionally include charging circuitry, and the AC coil 74 may be used to receive power from the external charger 22. Alternatively or additionally, the high-speed transceiver 90 may include charging circuitry, and the AC receiving coil 88 may be used to receive power from the external charger 22.

Additional details concerning the above-described and other IPGs may be found in U.S. Pat. No. 6,516,227, U.S. Pat. No. 6,993,384, and U.S. Pat. No. 7,539,538, which are expressly incorporated herein by reference. It should be noted that rather than an IPG, the SCM system 10 may alternatively utilize an implantable receiver-stimulator (not shown) connected to leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the modulation in accordance with the control signals.

Figure 5:
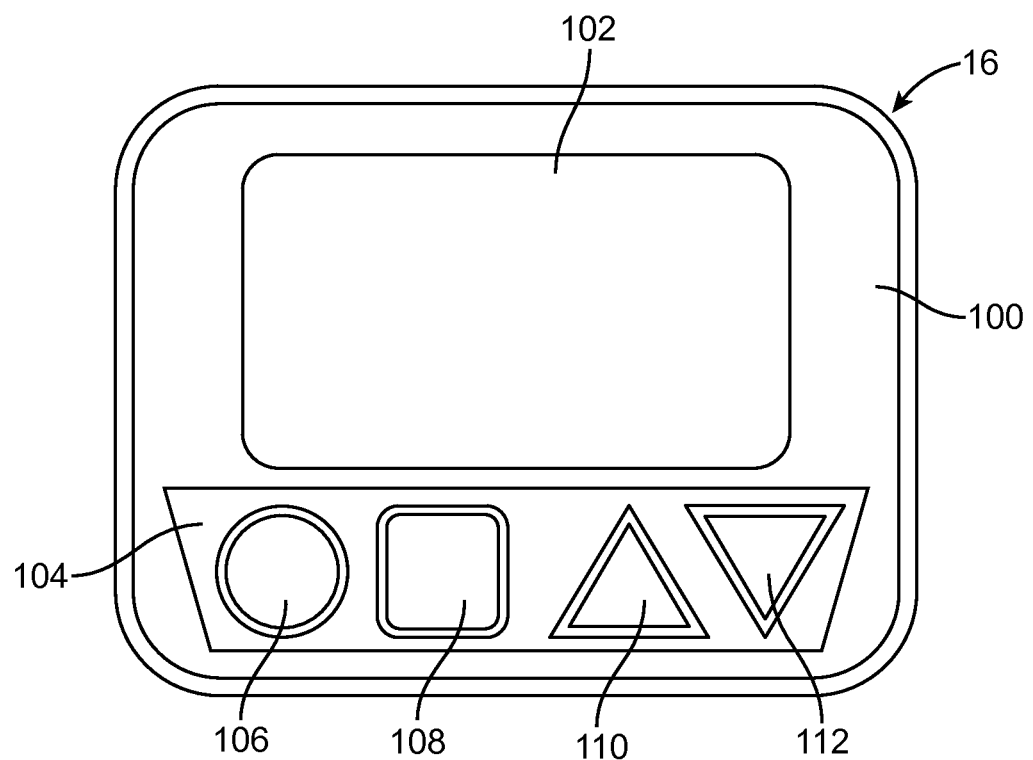
FIG. 5 is a plan view of a hand-held remote control (RC) that can be used in the SCM system of FIG. 1.

Referring now to FIG. 5, one exemplary embodiment of an RC 16 will now be described. As previously discussed, the RC 16 is capable of communicating with the IPG 14, CP 18, or ETM 20. The RC 16 comprises a casing 100, which houses internal componentry (including a printed circuit board (PCB)), and a lighted display screen 102 and button pad 104 carried by the exterior of the casing 100. In the illustrated embodiment, the display screen 102 is a lighted flat panel display screen, and the button pad 104 comprises a membrane switch with metal domes positioned over a flex circuit, and a keypad connector connected directly to a PCB. In an optional embodiment, the display screen 102 has touchscreen capabilities. The button pad 104 includes a multitude of buttons 106, 108, 110, and 112, which allow the IPG 14 to be turned ON and OFF, provide for the adjustment or setting of modulation parameters within the IPG 14, and provide for selection between screens.

In the illustrated embodiment, the button 106 serves as an ON/OFF button that can be actuated to turn the IPG 14 ON and OFF. The button 108 serves as a select button that allows the RC 16 to switch between screen displays and/or parameters. The buttons 110 and 112 serve as up/down buttons that can be actuated to increase or decrease any of modulation parameters of the pulse generated by the IPG 14, including the pulse amplitude, pulse width, and pulse rate. For example, the selection button 108 can be actuated to place the RC 16 in a "Pulse Amplitude Adjustment Mode," during which the pulse amplitude can be adjusted via the up/down buttons 110, 112, a "Pulse Width Adjustment Mode," during which the pulse width can be adjusted via the up/down buttons 110, 112, and a "Pulse Rate Adjustment Mode," during which the pulse rate can be adjusted via the up/down buttons 110, 112. Alternatively, dedicated up/down buttons can be provided for each stimulation parameter. Rather than using up/down buttons, any other type of actuator, such as a dial, slider bar, or keypad, can be used to increment or decrement the stimulation parameters.

Figure 6:
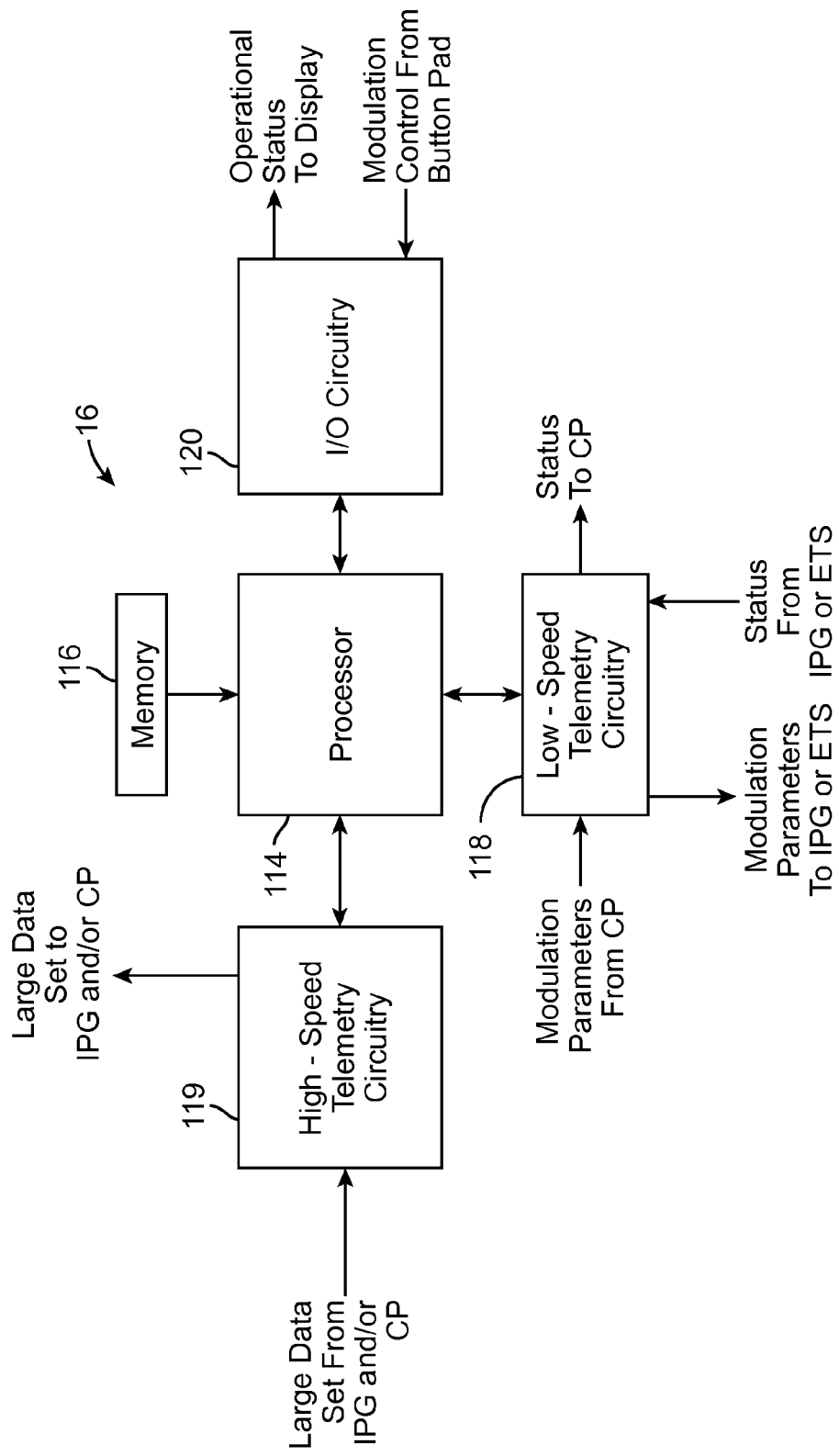
FIG. 6 is a block diagram of the internal components of the RC of FIG. 5.

Referring to FIG. 6, the internal components of an exemplary RC 16 will now be described. The RC 16 generally includes a processor 114 (e.g., a microcontroller), memory 116 that stores an operating program for execution by the processor 114, as well as modulation parameters, telemetry circuitry 118 for outputting modulation parameters to the IPG 14 and receiving status information from the IPG 14, and input/output circuitry 120 for receiving modulation control signals from the button pad 104 and transmitting status information to the display screen 102 (shown in FIG. 5). The telemetry circuitry 118 may be low-speed telemetry circuitry, and the RC 16 may optionally include high-speed telemetry circuitry 119 for outputting and receiving large data sets to and from the IPG 14 and/or the CP 18. Such large data sets may include non-programming data such as Magnetic Resonance Image (MRI) data, Computed Tomography (CT) data, clinical effects data, brain atlas transformation data, program usage data, battery history data, electrical parameter measurement data, lead configuration data, electrode configuration data, safety limit data, or the like. The low-speed telemetry circuitry 118 may be configured for communicating with the low-speed telemetry system 73 of the IPG, and the high-speed telemetry circuitry 119 may be configured for communicating with the high-speed telemetry system 87 of the IPG.

As well as controlling other functions of the RC 16, which will not be described herein for purposes of brevity, the processor 114 generates a plurality of modulation parameter sets that define the amplitude, phase duration, frequency, and waveform shape in response to the user operation of the button pad 104. These new modulation parameter sets would then be transmitted to the IPG 14 via the low-speed telemetry circuitry 118, thereby adjusting the modulation parameters stored in the IPG 14 and/or programming the IPG 14. The low-speed telemetry circuitry 118 can also be used to receive modulation parameters from the CP 18. Further details of the functionality and internal componentry of the RC 16 are disclosed in U.S. Pat. No. 6,895,280, which has previously been incorporated herein by reference.

As briefly discussed above, the CP 18 greatly simplifies the programming of multiple electrode combinations, allowing the user (e.g., the physician or clinician) to readily determine the desired stimulation parameters to be programmed into the IPG 14, as well as the RC 16. Thus, modification of the stimulation parameters in the programmable memory of the IPG 14 after implantation is performed by a user using the CP 18, which can directly communicate with the IPG 14 or indirectly communicate with the IPG 14 via the RC 16. That is, the CP 18 can be used by the user to modify operating parameters of the electrode array 26 near the spinal cord.

As shown in FIG. 3, the overall appearance of the CP 18 is that of a laptop personal computer (PC), and in fact, may be implemented using a PC that has been appropriately configured to include a directional-programming device and programmed to perform the functions described herein. Alternatively, the CP 18 may take the form of a mini-computer, personal digital assistant (PDA), smartphone, etc., or even a remote control (RC) with expanded functionality. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 to allow the optimum stimulation parameters to be determined based on patient response and feedback and for subsequently programming the IPG 14 with the optimum stimulation parameters.

Figure 7:
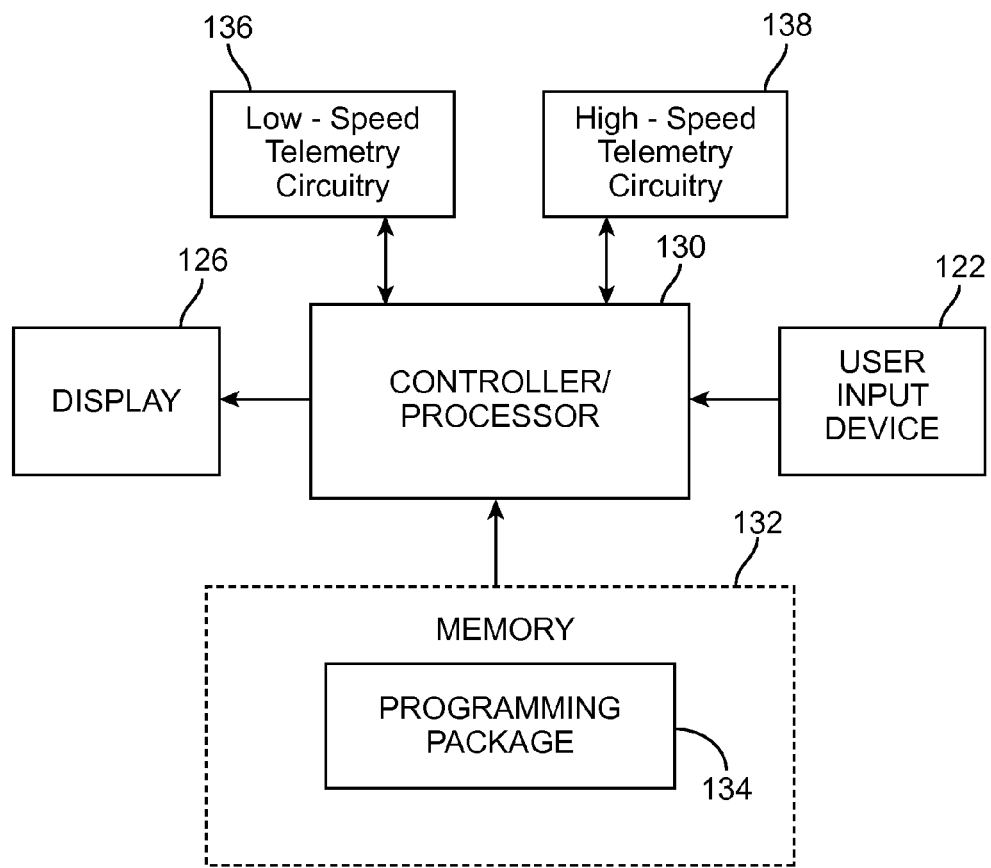
FIG. 7 is a block diagram of the internal components of a clinician's programmer (CP) used in the SCM system of FIG. 1.

Referring to FIG. 7, to allow the user to perform these functions, the CP 18 includes a standard user input device 122 (e.g., a keyboard, mouse, joystick, etc.) to allow a clinician to input information and control the process, and a display monitor 126 housed in a case. In the illustrated embodiment, the monitor 126 is a conventional screen. Alternatively, instead of being conventional, the monitor 126 may be a digitizer screen, such as touchscreen (not shown), and may be used in conjunction with an active or passive digitizer stylus/finger touch. The CP 18 further includes a controller/processor 130 (e.g., a central processor unit (CPU)) and memory 132 that stores a stimulation programming package 134, which can be executed by the controller/processor 130 to allow the user to program the IPG 14, and RC 16. Notably, while the controller/processor 130 is shown as a single device, the processing functions and controlling functions can be performed by a separate controller and processor.

Execution of the programming package 134 by the controller/processor 130 provides a multitude of display screens (not shown) that can be navigated through via use of the input device 122. These display screens allow the clinician to, among other functions, select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical stimulation energy output by the leads 12, and select and program the IPG 14 with stimulation parameters in both a surgical setting and a clinical setting. Further details discussing the above-described CP functions are disclosed in U.S. Patent Application Publication No. 2010/0010566, entitled "System and Method for Converting Tissue Stimulation Programs in a Format Usable by an Electrical Current Steering Navigator," and U.S. Patent Application Publication No. 2010/0121409, entitled "System and Method for Determining Appropriate Steering Tables for Distributing Stimulation Energy Among Multiple Neurostimulation Electrodes," which are expressly incorporated herein by reference.

The CP 18 further includes low-speed telemetry circuitry 136 for downloading stimulation parameters to the IPG 14 and RC 16 and for uploading stimulation parameters already stored in the memory 116 of the RC 16, or the memory 70 of the IPG 14, via the low-speed telemetry circuitry 118 of the RC 16 and/or the low-speed telemetry system 73 of the IPG 14. The CP 18 optionally includes high-speed telemetry circuitry 138 for downloading large data sets to the IPG 14 and/or RC 16, and for uploading large data sets stored in the memory 70 of the IPG 14 and/or the memory 116 of the RC 16 via the high-speed telemetry system 87 of the IPG 14 and/or the high-speed telemetry circuitry 119 of the RC 16.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. An implantable neuromodulation device, comprising:
a plurality of electrical terminals configured for being respectively coupled to a plurality of electrodes;
analog output circuitry configured for delivering electrical modulation energy to the electrical terminals in accordance with programming data from a first external control device; a low-speed telemetry system configured for receiving the programming data;
a high-speed telemetry system configured for receiving non-programming data from a second external control device; and
memory configured for storing the programming data and the non-programming data.

2. The implantable neuromodulation device of claim 1, wherein the low-speed telemetry system has a data transfer rate in the range of 2-800 kbits/sec, and the high-speed telemetry system has a data transfer rate in the range of 1-50 Mbits/sec.

3. The implantable neuromodulation device of claim 1, wherein the low-speed telemetry system has a first telemetry range, and the high-speed telemetry system has a second telemetry range greater than the first telemetry range.

4. The implantable neuromodulation device of claim 3, wherein the first telemetry range is 0.1-6 feet, and the second telemetry range is greater than 6 feet.

5. The implantable neuromodulation device of claim 1, wherein the non-programming data comprises at least one of Magnetic Resonance Image (MRI) data, Computed Tomography (CT) data, clinical effects data, and brain atlas transformation data.

6. The implantable neuromodulation device of claim 1, wherein the non-programming data comprises at least one of program usage data, battery history data, electrical parameter measurement data, lead configuration data, electrode configuration data, and safety limit data.

7. The implantable neuromodulation device of claim 1, wherein the first external control device and the second external control device are the same external control device.

8. The implantable neuromodulation device of claim 1, wherein the low-speed telemetry system is configured for transmitting the stored programming data to the first external control device, and the high-speed telemetry system is configured fir transmitting the stored non-programming data to the second external control device.

9. A neuromodulation system, comprising:
a first external control device configured for transmitting programming data;
a second external control device configured for transmitting non-programming data;
a plurality of electrodes; and
an implantable neuromodulation device comprising a plurality of electrical terminals coupled to the plurality of electrodes, analog output circuitry configured for delivering electrical modulation energy to the electrical terminals in accordance with the programming data from the first external control device, a low-speed telemetry system configured for receiving the programming data, a high-speed telemetry system configured for receiving the non-programming data from the second external control device, and memory configured for storing the programming data and the non-programming data.

10. The neuromodulation system of claim 9, wherein the low-speed telemetry system has a data transfer rate in the range of 2-800 kbits/sec, and the high-speed telemetry system has a data transfer rate in the range of 1-50 Mbits/sec.

11. The neuromodulation system of claim 9, wherein the low-speed telemetry system has a first telemetry range, and the high-speed telemetry system has a second telemetry range greater than the first telemetry range.

12. The neuromodulation system of claim 11, wherein the first telemetry range is 0.1-6 feet, and the second telemetry range is greater than 6 feet.

13. The neuromodulation system of claim 9, wherein the non-programming data comprises at least one of Magnetic Resonance Image (MRI) data, Computed Tomography (CT) data, clinical effects data, and brain atlas transformation data.

14. The neuromodulation system of claim 9, wherein the non-programming data comprises at least one of program usage data, battery history data, electrical parameter measurement data, lead configuration data, electrode configuration data, and safety limit data.

15. The neuromodulation system of claim 9, wherein the first external control device and the second external control device are the same external control device.

16. The neuromodulation system of claim 9, wherein the low-speed telemetry system is configured for transmitting the stored programming data to the first external control device, and the high-speed telemetry system is configured for transmitting the stored non-programming data to the second external control device.

* * * * *